US012127577B2

(12) United States Patent
Lacaze et al.

(10) Patent No.: US 12,127,577 B2
(45) Date of Patent: Oct. 29, 2024

(54) COMPOSITIONS RICH IN ARABINOXYLAN OLIGOSACCHARIDES

(75) Inventors: Guylaine Lacaze, Haillot (BE); Isabel Trogh, Burcht (BE); Bernard Genot, Villers-le-Bouillet (BE); Filip Arnaut, Roosdaal (BE)

(73) Assignee: Puratos N.V., Groot-Bugaarden (BE)

( * ) Notice: Subject to any disclaimer, the term of this patent is extended or adjusted under 35 U.S.C. 154(b) by 1232 days.

(21) Appl. No.: 13/695,672

(22) PCT Filed: May 3, 2011

(86) PCT No.: PCT/EP2011/057005
§ 371 (c)(1),
(2), (4) Date: Dec. 12, 2012

(87) PCT Pub. No.: WO2011/138303
PCT Pub. Date: Nov. 10, 2011

(65) Prior Publication Data
US 2013/0101699 A1    Apr. 25, 2013

(30) Foreign Application Priority Data
May 3, 2010 (FR) ...................... 1001893

(51) Int. Cl.
| | | |
|---|---|---|
| *A23L 33/22* | (2016.01) | |
| *A21D 2/18* | (2006.01) | |
| *A21D 8/04* | (2006.01) | |
| *A21D 10/00* | (2006.01) | |
| *A23L 7/10* | (2016.01) | |
| *A23L 7/104* | (2016.01) | |
| *A23L 33/10* | (2016.01) | |
| *C12P 19/04* | (2006.01) | |

(52) U.S. Cl.
CPC .............. *A23L 33/22* (2016.08); *A21D 2/18* (2013.01); *A21D 8/045* (2013.01); *A21D 10/002* (2013.01); *A23L 7/104* (2016.08); *A23L 7/115* (2016.08); *A23L 33/10* (2016.08); *C12P 19/04* (2013.01)

(58) Field of Classification Search
None
See application file for complete search history.

(56) References Cited

U.S. PATENT DOCUMENTS

| | | | | |
|---|---|---|---|---|
| 4,305,963 A | * | 12/1981 | Nakagawa | |
| 5,108,766 A | * | 4/1992 | Gelinas ................. | A23L 27/24 426/43 |
| 6,783,780 B1 | * | 8/2004 | De Jong ............ | A61K 35/745 424/93.3 |
| 2006/0165848 A1 | * | 7/2006 | Bryckaert ............ | A21D 8/045 426/94 |
| 2008/0131556 A1 | * | 6/2008 | De Simone ........... | A21D 8/042 426/20 |
| 2010/0035302 A1 | * | 2/2010 | Broekaert ................ | C12P 7/10 435/72 |
| 2010/0040731 A1 | * | 2/2010 | Aerts et al. | |

FOREIGN PATENT DOCUMENTS

| | | | |
|---|---|---|---|
| GB | 2464769 | * 12/2008 | ........... A23K 20/163 |
| WO | WO 91/19782 | 12/1991 | |
| WO | WO 92/01793 | 2/1992 | |
| WO | WO 92/17573 | 10/1992 | |
| WO | WO 94/21785 | 9/1994 | |
| WO | WO 2006/002495 A1 | 1/2006 | |
| WO | WO 2008/000050 A2 | 1/2008 | |
| WO | WO 2008/087167 A2 | 7/2008 | |
| WO | WO 2009/117790 A2 | 10/2009 | |
| WO | WO 2009/158588 A1 | 12/2009 | |
| WO | WO 2010/081870 A1 | 7/2010 | |

OTHER PUBLICATIONS

Butt, et al. 2008. Xylanases and their applications in baking industry. *Food Technology and Biotechnology*, 46(1):22-31.
Corsetti, et al. 2000. Combined effect of sourdough lactic acid bacteria and additives on bread firmness and staling. *Journal of Agricultural and Food Chemistry*, 48:3044-3051.
Courtin, et al. 2000. Determination of reducing end sugar residues in oligo- and polysaccharides by gas-liquid chromatography. *Journal of Chromatography A*, 866:97-104.
Katina, et al. 2006. Effects of sourdough and enzymes on staling of high-fibre wheat bread. *Food Science and Technology*, 39(5):479-491.
International Search Report and Written Opinion of the International Searching Authority mailed Oct. 11, 2011, for International Application No. PCT/EP2011/057005 filed May 3, 2011.
Gebruers, et al. 2008. Variation in the content of dietary fiber and components thereof in wheats in the HEALTHGRAIN diversity screen. *J. Agric. Food Chem.*, 56:9740-9749.
Loosveld, et al. 1997. Contents and structural features of water-extractable arabinogalactan in wheat flour fractions. *J. Agric. Food Chem.*, 45:1998-2002.
Nyström, et al. 2008. Phytochemicals and dietary fiber components in rye varieties in the HEALTHGRAIN diversity screen. *J. Agric. Food Chem.*, 56:9758-9766.

(Continued)

*Primary Examiner* — Donald R Spamer
*Assistant Examiner* — Philip A Dubois
(74) *Attorney, Agent, or Firm* — Knobbe, Martens, Olson & Bear, LLP

(57) ABSTRACT

A method for preparing a liquid composition having a high arabinoxylan oligosaccharides content (AXOS), the product obtained by this method, and its use in food applications, in particular in baked products.

14 Claims, No Drawings

(56) References Cited

OTHER PUBLICATIONS

Trogh, et al. 2004. Isolation and characterization of water-extractable arabinoxylan from hull-less barley flours. *Cereal Chem.,* 81(5):576-581.
Guilloux et al. 2009. Production of Arabinoxylan-oligosaccharides from Flaxseed (*Linum usitatissimum*), *Journal of Agricultural and Food Chemistry,* 57:11308-11313.

* cited by examiner

COMPOSITIONS RICH IN ARABINOXYLAN OLIGOSACCHARIDES

This application is the U.S. National Phase of Application No. PCT/EP2011/057005 entitled "COMPOSITIONS RICH IN ARABINOXYLAN OLIGOSACCHARIDES" filed May 3, 2011, and published in English on Nov. 10, 2011 as WO 2011/138303 A1 which claims the benefit of French Application No. 1001893 filed May 3, 2010.

FIELD OF THE INVENTION

The invention relates to compositions for food applications more particularly suitable for baked products.

More particularly, the invention relates to a method for preparing a liquid composition having a high arabinoxylan oligosaccharides content (AXOS), to the product obtainable by this method, and its use in food applications, in particular in baked products.

BACKGROUND OF THE INVENTION AND STATE OF THE ART

The health benefits ascribed to prebiotics include increased solubility and bio-availability of minerals (e.g. calcium, magnesium, iron, zinc), suppression of potentially pathogenic bacteria in the colon, reduced levels of triglycerides and cholesterol in the blood, stimulation of the satiety response, improved stool transit, reduced risk for colon cancer, etc.

Arabinoxylan (AX), also referred to as pentosan, is a non-starch polysaccharide and major constituent of cereal grains.

AXOS (Arabinoxylan oligosaccharides) have been shown to have prebiotic properties (WO2006/002495).

AXOS can be produced by the action of endoxylanases and/or chemicals and/or by physical treatment on AX, such as the AX present in cereals. The production of shorter AX fragments through endoxylanase action on AX already occurs to a limited extent during current commercial making of bread and pastry products (baked products), when endoxylanases are added during the mixing step.

However, due to the low doses of endoxylanases used in commercial bread- and pastry-making, the AXOS levels in current bread and pastry products are not sufficiently high to exert beneficial prebiotic effects upon ingestion of a regular portion of such product, and moreover, the average DP is too high so as for the AXOS to exert its optimal prebiotic effect.

All methods and processes described in the prior art disclose partial solubilisation and/or hydrolysis of the AX present in the substrate used or in the (dough) formulation.

In humans, desired physiological effects, such as the increase in the number of Bifidobacteria present in the faeces, the reduction of ammonia excretion through urine and the increased excretion via faeces, are observed at high daily intake doses.

To achieve a high level of AXOS aiming at exerting the prebiotic effect it is possible to use a substantial amount of enzymatically treated AX-containing raw material.

For instance, WO2008/087167 describes a method to increase in a baked product the level of AXOS with an average DP of 5 to 50 that comprises a step of preparing a dough with flour having a total AX content of at least 2.5% and a step of adding to the dough a thermophilic endoxylanase in a relatively high amount. However, this approach is limited to baked product comprising non-refined flour and/or milling fractions enriched in bran, which can impair the consumer's preference for such products.

Purified or semi-purified AXOS preparations have been described. However their costs render their use in food applications such as baking uneconomical.

Furthermore due to the viscosity of the products enriched in AXOS obtained after enzymatic treatment, it is not possible to obtain products in a dry/powder form using the regular equipment of the food/food ingredients industry.

There is therefore a need for new products or processes able to provide high amounts of AXOS with a DP lower than 50 in an economical way.

SUMMARY OF THE INVENTION

One aspect of the present invention is a method for preparing a liquid composition having an arabinoxylan oligosaccharides content (AXOS) higher than 8% (w:w on dry matter), preferably higher than 9, 10, 11, 12 or even 13 weight percent of the dry matter, said AXOS having an average degree of polymerization (DP) comprised between 5 and 50, preferably between 5 and 35, even more preferably between 5 and 25, said method comprising the steps of:
  providing an aqueous mixture comprising grain milling fraction(s) (or consisting of grain milling fraction(s) and water);
  fermenting said mixture by lactic acid bacteria, or by both lactic acid bacteria and yeasts;
  incubating said mixture with an endoxylanase, preferably an exogenous endoxylanase, for hydrolyzing the arabinoxylan of said grain milling fraction(s).

Preferably, the grain milling fraction(s) used in the method of the present invention comprise(s) (or is/are) cereal grain milling fraction(s), preferably cereal bran, more preferably rye bran or wheat bran.

Preferably, the initial arabinoxylan content of the grain milling fraction(s) is higher than 10%, preferably higher than 15% (w:w; on dry matter).

The present method possibly further comprises a step of pasteurization.

Advantageously, the incubation step and the fermentation step of the method of the invention are performed concomitantly (i.e concurrently or simultaneously).

Alternatively, the incubation step is performed before the fermentation step.

Still alternatively the incubation step is performed after the fermentation step.

Advantageously, the incubation step and the pasteurization step are performed concomitantly and preferably the endoxylanase (acting optimally during the incubation step) is a thermostable endoxylanase.

Preferably, the incubation step is performed at a temperature of 10° C. higher or lower than the optimal temperature of the enzyme used, more preferably at the optimal temperature of the enzyme used.

Possibly, the present method further comprises a step of drying the resulting composition, in particular obtained after fermentation, incubation (and optionally pasteurization) steps.

Another aspect of the present invention is a composition obtainable by a method according to the invention.

A related aspect of the present invention is liquid composition comprising:
  fermented grain milling fraction(s),
  lactic acid bacteria and possibly/optionally yeasts,
  endoxylanase, said composition having an arabinoxylan oligosaccharides content (AXOS), higher than 8% (w:w on dry matter), said AXOS being enzymatically released (or extracted) from said grain milling fraction(s), and said AXOS having an average degree of polymerization (DP) comprised between 5 and 50.

Preferably, the composition of the invention has an AXOS content higher than 10 weight percent of the dry matter, more preferably higher than 11, 12 or even 13 w. % of the dry matter.

Preferably in this composition, the fermented grain milling fraction(s) comprise(s) (or is/are) fermented cereal grain milling fraction(s), preferably fermented cereal bran, more preferably fermented rye bran or fermented wheat bran.

More preferably, the composition of the present invention has a dry matter content higher than 18%, even more preferably higher than 20%.

Preferably, the composition of the present invention has an acidic pH, preferably a pH comprised between about 2.9 and about 4.2, preferably between about 3.0 and 4.0, more preferably between about 3.1 and 3.8.

Advantageously, the composition of the present invention has a (dynamic) viscosity lower than about 150 Pa s (150000 centipoise; cP), preferably lower than 100 Pa s (100000 cP), more preferably lower than about 35 Pa s (35000 cP), even more preferably lower than about 10 Pa s (10000 cP).

Advantageously, the (dynamic) viscosity of the composition is measured at 30° C.

Possibly, the (dynamic) viscosity of the composition is measured using Brookfield viscosimeter DV-II+ with a LV4 spindle rotating at 1.5 rpm.

Possibly, the composition of the present invention is pasteurized and/or dried.

Advantageously, the AXOS obtained by the method of the invention and/or the AXOS present in the composition of the invention have an average DP comprised between 5 and 35, and even more preferably comprised between 5 and 25.

More preferably, the average DP of AXOS is the mean DP.

Advantageously the water content of the aqueous mixture of the present method or of the present composition, is comprised between about 90% and 40% (w/w) (corresponding to a dry matter comprised between about 10% and 60%), more preferably between about 82% and 50% (corresponding to a dry matter comprised between about 18% and 50%), still more preferably between about 80% and 60% (corresponding to a dry matter comprised between about 20% and 40%), and even more preferably between 80% and 70% (corresponding to a dry matter comprised between about 20% and 30%).

Advantageously the pH of the present composition is acidic, preferably comprised between about 2.9 to about 4.2, more preferably between about 3.0 and 4.0, still more preferably between 3.1 and 3.8.

Preferably the lactic acid bacteria used in the method of the invention, or that are in the composition of the invention are *Leuconostoc* or lactobacilli, preferably selected from the group consisting of *Lactobacillus plantarum, Lactobacillus brevis, Lactobacillus sanfrancisciensis* and *Lactobacillus reuterii*, being most preferably *Lactobacillus plantarum*.

The preferred yeast used in the present method and/or part of the present composition is *S. cerevisiae*.

Advantageously, the endoxylanase of the method and of the composition is a thermostable endoxylanase, possibly derived from fungal or bacterial species. More particularly, said endoxylanase is a composition comprising one or more (purified or partially purified) enzyme(s) exhibiting endoxylanolytic activity.

Another aspect of the present invention is a premix or a complete mix comprising this composition.

The present invention further relates to the use of the composition as sourdough or as a sourdough product and/or for making baked products.

DETAILED DESCRIPTION OF THE INVENTION

The inventors have found a method and a composition that overcome the limitations of the prior art.

In general, AX from cereals consists of a backbone of beta-(1-4)-linked D-xylopyranosyl residues (xylose), some of which are mono- or disubstituted with alpha-L-arabinofuranosyl residues (arabinose). In addition, other substituents, such as ferulic acid, coumaric acid, acetic acid or (methyl)glucuronic acid, can be coupled to some of the xylose and/or arabinose residues of AX.

AX can be divided into either water-extractable AX (WE-AX) and water-unextractable AX (WU-AX), both of which have a similar structure but differ in the level of cross-linking with other natural polymers.

Levels of AX in cereals vary depending on the plant species, genetic and environmental parameters, and on the type of fraction from the grain kernel. Wheat and rye flour contain in total about 1% to 3% and 3 to 5% AX, respectively. In the bran fractions, total AX contents range from 12% to 22% and 12% to 15%, respectively (Gebruers et al, 2008, J. Agric. Food Chem. 56, p. 9740; Nyström et al, 2008, J. Agric. Food Chem. 56. p. 9756).

More particularly, the inventors have developed a liquid composition rich in AXOS and a method to obtain such liquid composition rich in AXOS from an AX-rich source, with a DP lower than 50 and has an acceptable viscosity.

In the context of the present invention the "AX-rich component" or "AX-rich source" refers to any grain, or any grain milling fraction, including bran, flour, wholegrain flour, which contains 10% or more than 10% AX (w/w dry matter).

The term "grain", in the context of the present invention, refers to seed of a plant, such as but not limited to cereals or pseudo-cereals, with or without remnants of the fruit and with or without remnants of the flower.

The term "cereal", in the context of the present invention, refers to plants of the botanical family of the Poaceae, including but not limited to species such a wheat, barley, oat, spelt, rye, sorghum, maize, triticale, millet, teff and rice.

Pseudocereals are broadleaf plants (non-grasses) that have a similar chemical composition and similar way of use as cereals. Examples of pseudocereals are amaranth, quinoa and buckwheat.

The term "milling fraction" or "grain milling fraction", in the context of the present invention, refers to all or part of the fractions resulting from mechanical reduction of the size of grains, through, as examples but not limited to, cutting, rolling, crushing, breakage or milling, with or without fractionation, through, as examples but not limited to, sieving, screening, sifting, blowing, aspirating, centrifugal sifting, windsifting, electrostatic separation, or electric field separation.

The term "bran" in the context of the present invention, refers to a milling fraction comprising aleurone and/or pericarp as the major fraction, or preferably comprising mainly aleurone and/or pericarp.

Possibly, this bran comprising as major fraction, or mainly aleurone and/or pericarp, can further comprise any or all of the tissues selected from the group consisting of sepals, petals, nucellar epidermis and seed coat.

The bran used in the present invention can be extruded or pelletised, followed by milling or any another form of physical homogenisation.

Advantageously, the milling fraction(s), and more particularly the bran used in the present invention have/has an endogenous AX content of at least 10% (w:w), preferably of at least 15% (w:w) on dry matter.

The term "sourdough" in the context of the present invention refers to a dough fermented by lactic acid bacteria and possibly yeast, having a characteristic acidic flavour due to production of lactic acid and/or acetic acid by the lactic acid bacteria, and some minor components, as well as the typical flavour top-notes produced by the yeast, if present.

The term "sourdough product" refers to the sourdough as defined above, which is stabilized in one or another way (e.g. through drying, pasteurization, cooling, freezing, . . . ) so that this product can be added to a regular dough, thereby replacing the in-bakery produced pre-fermentation.

The term "living cells" or "starter culture" in the context of the present invention refers to living lactic acid bacteria and optionally yeast that are used for the fermentation step.

Preferably lactic acid bacteria are chosen among acid forming bacteria such as *Leuconostoc* or lactobacillus, preferably selected from the group of *Lactobacillus plantarum, Lactobacillus brevis, Lactobacillus sanfrancisciensis* and *Lactobacillus reuterii*.

Yeast strains are advantageously chosen among *Saccharomyces cerevisiae* and *Saccharomyces exiguus*.

Starter cultures may be under dry or liquid form before being used. Dry starters may be rehydrated before use, for example by suspending the starter in water containing sugar and salt.

In the context of the present invention the term "endoxylanase" refers to an enzyme or a mixture of enzymes that is/are able to hydrolyze internal glycosyl bonds linking xylose residues in xylose-containing polysaccharides. Such glycosyl bonds can be for instance the beta-1,4-glycosyl bond in beta-D-xylopyranosyl-1,4-beta-D-xylopyranosyl units of such polysaccharides.

Endoxylanases are preferably derived from fungal (e.g. species of *Aspergillus, Penicillium, Disporotrichum, Neurospora, Fusarium, Humicola, Trichoderma*) or bacterial species (e.g. species of *Bacillus, Aeromonas, Streptomyces, Nocardiopsis, Thermomyces, Thermotoga, Thermomonospora, Nonomuraea, Pseudoalteromonas*) (see for example WO92/17573, WO92/01793, WO91/19782, WO94/21785).

Commercially available purified or partially purified endoxylanase preparations include Belase™ B210, Belase™ B218 (Puratos); Shearzyme™, Biofeed Wheat™, Pentopan™ Mono BG, Pentopan™ 500 BG and Pulpzyme™ (Novozymes); Ecopulp™, Rohament GE™, Veron HTX™, Veron™ 191 and Veron™ Special (AB Enzymes); Multifect™ endoxylanase, Multifect™ 720, Spezyme™ CP, Grindamyl™ H640, and Grindamyl™ Powerbake™ (Danisco).

Endoxylanase activity may be determined by methods well known in the art.

Particularly suited is a method using the property of endoxylanases to hydrolyze xylan as substrate. The hydrolysis reaction liberates reducing sugars that cause a typical color to be developed by reaction with dinitrosalicylic acid (DNS). The color intensity at 570 nm is directly proportional to the endoxylanase activity in the sample. One UI (international unit) of endoxylanase is defined as the amount of enzyme that liberates 1 μmole of reducing sugars (as xylose equivalent) per minute from birchwood xylan in the conditions of the test.

An alternative method is Azo-Xylan method (Megazyme, Ireland). The substrate is Azo-oat xylan, a purified oat xylan dyed with Remazolbrilliant Blue R. Hydrolysis by endoxylanase produces water soluble dye fragments released after ethanol precipitation of the unhydrolyzed substrate. The rate of release of these fragments is followed by the increase of absorbance at 590 nm and can be related directly to the enzyme activity expressed in AXU/g or ml.

According to the present invention the grain milling fraction(s), more particularly the bran, is/are firstly suspended in a suitable liquid, preferably water. Dry matter of this aqueous mixture is preferably between 20 and 40%. The aqueous mixture is fermented by the addition of living cells comprising (or consisting of) lactic acid bacteria and optionally yeast and incubation for a period between 10 and 50 hours, preferably between 15 and 45 hours, more preferably between 20 and 30 hours and at a temperature between 25° C. and 40° C., preferably between 25° C. and 35° C.

Optionally, during incubation, the mixture is mixed regularly or at various intervals.

The pH at the end of the fermentation is lower than 4.2, preferably lower than 4.0, more preferably lower than 3.8.

Still according to the present invention the treatment with an endoxylanase may be performed before, simultaneously with, or after the fermentation step.

In one aspect of the present invention, the endoxylanase and the living cells comprising (or consisting of) lactic acid bacteria and optionally yeast are added to the aqueous mixture, which is therefore concomitantly fermented and incubated. This fermentation/incubation step is optionally followed by a further incubation step, preferably at a temperature close to the optimal temperature of the endoxylanase.

In another aspect of the present invention the aqueous mixture of grain milling fraction(s) is incubated with the endoxylanase, preferably at a temperature close to the optimal temperature of the endoxylanase, then the living cells comprising or consisting of lactic acid bacteria (and optionally yeast) are added and the mixture is fermented.

In another aspect of the present invention the aqueous mixture of grain milling fraction(s) is fermented by the living cells comprising or consisting of lactic acid bacteria (and optionally yeast), then the endoxylanase is added and the mixture is incubated preferably at a temperature close to the optimal temperature of the endoxylanase.

At the end of the fermentation and/or of the incubation with the enzyme, the composition may be inactivated by a heating step.

Pasteurization is a preferred method for inactivation. An example of pasteurization is a treatment at 75° C. for 30 min.

An incubation performed at temperatures of 70° C. or above has a similar effect as pasteurization (for instance a treatment at 70° C. for 1 to 5 hours).

The incubation step (possibly serving as pasteurization step) is advantageously performed at a temperature between the optimal temperature of the endoxylanase minus 15° C. and the optimal temperature plus 15° C., more preferably at a temperature between the optimal temperature minus 10° C. and the optimal temperature plus 10° C., even more preferably at a temperature closed to the optimal temperature, for a period of time between 1 and 10 hours, preferably between 3 and 8 hours, more preferably between 4 and 6 hours.

In a method of the invention at least 50%, preferably, 60%, more preferably 70%, even more preferably 80% of the initial AX of the grain milling fraction(s) are solubilised to form AXOS.

A liquid composition according to the invention or a liquid composition obtainable by a method according to the invention comprises:
fermented grain milling fraction(s),
lactic acid bacteria and possibly (optionally) yeasts, endoxylanase;
has an arabinoxylan oligosaccharides content (AXOS), higher than 8% (w:w on dry matter); said AXOS being enzymatically released (or extracted) from said grain milling fraction(s), and said AXOS having an average DP comprised between 5 and 50, more preferably comprised between 5 and 35, and even more preferably comprised between 5 and 25.

Preferably, the composition of the invention has an AXOS content higher than 10% (w:w on dry matter), more preferably higher than 11, 12 or even 13%.

Preferred liquid compositions contains more than 18%, more preferably more than 20% dry matter.

Preferred liquid compositions have a viscosity lower than 150000 cP (i.e. 150 Pa s).

The (dynamic) viscosity may be measured using several suitable devices and/or methods.

In the present invention, the (dynamic) viscosity is preferably measured at 30° C., possibly using a Brookfield viscosimeter DV-II+ with a (viscosities higher than 10000 cP-10 Pa s) LV4 spindle rotating at 1.5 rpm or (viscosities below 10000 cP-10 Pa s) with a spindle LV2 at 3 rpm.

The inventors have found that the combination of the steps of the present invention generates compositions (rich in AXOS) that are pourable, easily pumpable and easily dryable with conventional equipment used in the food industry.

Dry/solid form such as powder may therefore be obtained by subjecting the liquid composition to a drying step such a spray drying or drum drying. Preferred dry matter of the solid/powdered composition is more than 90%, preferably 92%.

Possibly this composition is used as an ingredient for the preparation of food products. Example of preparation is the preparation of the dough for a baked product.

Also provided is a baked product comprising a composition according to the invention.

A baked product of the present invention comprised a unleavened, a yeast-leavened or a chemically leavened baked product, the major ingredient of which is flour derived from cereal grains. The baked product of the invention can also contain fat or fat replacer, sugar, eggs, gluten, starch, hydrocolloids, enzymes, emulsifiers, oxidizing or reducing compounds, prebiotics compounds and/or an improver. Examples of baked products are bakery products and patisserie products.

Advantageously, the composition of the present invention is part of an improver, a premix or a complete mix for baked products, more particularly for bakery products.

An improver according to the present invention comprises a composition of the invention and further comprises ingredients and/or technological aids used for their beneficial properties during the preparation of baked products and/or after baking. These properties comprise but are not limited to aspect, volume, freshness, conservation, color, structure or short bite of the baked products.

The term "premix" refers typically to an improver composition wherein the concentration in "active" component is lower than in a bakery improver. Typically a premix is used at an higher dose than a improver (weight/weight of flour).

The term "complete mix" refers typically to a composition comprising all the ingredients needed to prepare a dough that can be baked to obtain a baked product, generally with the exception of water. In particular when the leavening agent is a biological agent, more particularly baking yeast, it can also be excluded from the complete mix.

A complete mix according to the invention comprises a composition of the invention and all the ingredients needed to prepare a dough that can be baked to obtain a baked product.

The invention will be described in the following non-limiting examples.

EXAMPLES

Example 1

Enzymes Used:

*Nonomuraea flexuosa* Endoxylanase contains 49500 AXU/ml as determined by the AZO-xylan method (Megazyme) at 60° C. pH 6.0. Belase™ B210 (endoxylanase *Bacillus subtilis*—Puratos) contains 210 U/g as determined by the reducing sugars method at 30° C. pH 4.5.

*Pseudoalteromonas haloplantis* endoxylanase contains 300 U/g as determined by the reducing sugars method at 25° C. pH 6.5.

Grain milling fraction(s) having an AX content higher than or equal to 10% was/were mixed with water, inoculated with lactic acid bacteria (*Lactobacillus plantarum*) and possibly with yeast (*Saccharomyces cerevisiae*) and subjected to fermentation.

Enzyme(s) was/were added before, simultaneously with or after fermentation.

The incubation step was performed at a temperature close to the optimal temperature of the enzyme.

At the end of the process the pH and the viscosity of the liquid compositions were determined. The compositions were treated at 90° C. for 30 minutes and stored at −20° C. until further processing. Samples of 15-20 g of were defrozen and lyophilized.

The performed analyses were the following:
Determination of the pH:
pH is measured on the composition with a pH-meter Handylab 1 (Schott) equipped with a pH-electrode InLab 419 (Mettler-Toledo)
Determination of the Viscosity
The viscosity is measured with a viscosimeter Brookfield DV-II+, with a spindle LV2 at 3 rpm for viscosities below 10000 cp (10 Pa s) and with a spindle LV4 at 1.5 rpm for viscosities higher than 10000 cp (10 Pa s). For these measures, the temperature is fixed at 30° C.
Determination of the Total AX Content:
Lyophilized samples (15 to 50 mg) were firstly hydrolyzed in 2.0 M trifluoroacetic acid (5.0 ml) at 110° C. for 60 min.

The total content of monosaccharides (expressed in % dry matter (DM) on composition) was determined by gas-liquid chromatography of alditol acetates obtained after sample hydrolysis, reduction and acetylation of the resulting monosaccharides as described (Trogh et al. Cereal Chem., 2004, 81(5), 576-581).

Total AX (% dry matter on composition)=0.88×[(% arabinose$_{total}$−0.7×% galactose$_{WE}$×% soluble fraction on composition)+% xylose$_{total}$]

Determination of the Water-Extractable Arabinoxylan (WE-AX):

Lyophilized sample was suspended in water (1/20:w/w). After 30 min at 90° C., the suspension was cooled and centrifuged (10000 g; 15 min, 4° C.). The supernatant was used to measure the amounts of water-extractable monosaccharides.

This supernatant (2.5 ml) was firstly hydrolyzed in 4.0 M trifluoroacetic acid (2.5 ml) at 110° C. for 60 min and further treated as above.

WE-AX (% dry matter on soluble fraction of composition)=$0.88 \times [(\% \text{ arabinose}_{WE}-\% \text{ arabinose}_{free,WE}-0.7 \times \% \text{ galactose}_{WE})+(\% \text{ xylose}_{WE}-\% \text{ xylose}_{free,WE})]$ Determination of Reducing End Sugar Residues and Free Monosaccharide Contents:

Reducing end sugar residues ($_{red}$) of supernatant mentioned above were estimated by gas-liquid chromatography of alditol acetates as described by Courtin et al. 2000 (J. Chromatogr. A, 866, 97-104).

The monomeric or free monosaccharide ($_{free}$) analysis was similar to that of reducing end monosaccharides, except that, after reduction, samples were immediately acetylated without hydrolyzing them first (Courtin et al. 2000).

Determination of Degree of Polymerization (DP) of AX/AXOS:

DP=$(\% \text{ arabinose}_{WE}-\% \text{ arabinose}_{free,WE}\% \text{ xylose}_{WE}-\% \text{ xylose}_{free,WE})/(\% \text{ xylose}_{red,WE}-\% \text{ xylose}_{free,WE})$.

Determination of AXOS Levels:

AXOS (% dry matter on composition)=WE-AX (% DM on soluble fraction of composition)×% soluble fraction in composition Determination of AX Solubilization Level Solubilization of AX (%)=(% AXOS/% total AX)× 100

In all cases, arabinose content was corrected for the presence of arabinogalactan-peptide, based on a arabinose:galactose ratio of 0.7, and with the assumption that all the arabinogalactan-peptide is present in the aqueous extract and that galactose in the aqueous extract originates solely from arabinogalactan-peptide (Loosveld et al., J. Agric. Food chem., 1997, 45, 1998-2002.

Results are presented in Table 2. These results show that a combination of fermentation and enzymatic treatment allows the obtaining of an acidic composition rich in AXOS with favorable DP, level and viscosity.

TABLE 1

| | Process steps | | A | B | C | D | E | F | G | I | J | K | L | M° | N° | O° |
|---|---|---|---|---|---|---|---|---|---|---|---|---|---|---|---|---|
| Mix | Rye bran(VK Roggen) | 140 g | X | X | X | X | X | X | X | X | X | X | X | X | | X |
| | Wheat bran | 140 g | | | | | | | | | | | | | X | |
| | Water | 410 g | X | X | X | X | X | X | X | X | X | X | X | X | X | X |
| | Endoxylanase N. flexuosa | 0.21 ml | X | X | | | X | X | | | | | | | | X |
| | Belase ™ B210 | 1.4 g | | | | | | | | X | X | | | | | |
| | Endoxylanase P. haloplanktis | 1.4 g | | | | | | | | | | | X | | | |
| | Lactobacillus plantarum (strain LACTOL) | 1.4 10$^9$ CFU | | | | X | X | X | X | X | X | X | X | X | | |
| | Cream yeast(S. cerevisiae DM 18%) | 6 g | | | | | | | | | | X | X | | | |
| Incubation 5 h 70° C. | | | | | | | | | | | | | | | | X |
| Addition of L. plantarum | | 1.4 10$^9$ CFU | | | | | | | | | | | | | | X |
| Fermentation 24 h 30° C. 100 rpm | | | | | | X | X | | | | | | | | | |
| Fermentation 48 h 30° C. 100 rpm | | | | | | | | X | X | X | X | X | X | | X | X |
| Fermentation 48 h 25° C. 100 rpm | | | | | | | | | | | | | | X | | |
| pH adjust. (3.5 with lactic acid) | | | | | | X | | | | | | | | | | |
| Addition Endoxylanase N. flexuosa | | 0.21 ml | | | | | X | | | | | X | | X | | |
| Incubation 5 h 70° C. | | | X | X | X | | X | | X | | | | X | | X | |
| Incubation 5 h 45° C. | | | | | | | | | | | | X | | | | |

°these compositions were obtained in a separate experiment

TABLE 2

| | Results | | | | | | | | | | | | | | |
|---|---|---|---|---|---|---|---|---|---|---|---|---|---|---|---|
| | A | B | C | D | E | F | G | I | J | K | L | M° | N° | O° |
| Total AX (% DM on composition) | 19.7 | 19.3 | 20.4 | 21.1 | 20.7 | 19.3 | 19.9 | 18.7 | 18.3 | 19.6 | 19.8 | 16.7 | 20.8 | 16.7 |
| AXOS (% DM on composition) | 3.5 | 11.0 | 12.8 | 4.7 | 13.6 | 10.3 | 10.3 | 10.3 | 10.6 | 5.8 | 13.7 | 12.01 | 11.9 | 14.7 |
| DP-AX/AXOS | 269 | 8 | 9 | 318 | 8 | 9 | 8 | 10 | 9 | 193 | 9 | 12 | 10 | 13 |
| AX solubilization (%) | 18 | 57 | 63 | 22 | 66 | 54 | 52 | 55 | 58 | 29 | 69 | 72 | 58 | 88 |
| pH of the composition | 6.1 | 6.08 | 3.67 | 3.74 | 3.78 | 3.54 | 3.78 | 3.39 | 3.41 | 3.43 | 3.41 | 3.53 | 3.61 | nd |
| Viscosity (cP) | 127000 | nd | 268000 | Nd | nd | 2040 | 2769 | nd | nd | nd | nd | nd | nd | nd |
| Viscosity (Pa s) | 127 | nd | 268 | Nd | nd | 2.04 | 2.77 | nd | nd | nd | nd | nd | nd | nd | nd: not determined
DM: dry matter

Control Conditions (See Further Above Table 1):

A: A mixture of Rye bran and water was heated for 5 h at 70° C. for mimicking the incubation step and/or the pasteurization step.

As shown in Table 2, the resulting DP of AX is too high and is not acceptable for the intended use and/or for prebiotic purposes.

Effects of the Addition of an Endoxylanase

B: same as A but to the mixture is added *N. Flexuosa* endoxylanase (a thermostable endoxylanase) and an incubation step is performed for 5 h at 70° C.

The DP of AX was considerably reduced, but the viscosity was increased.

C: same as B, but the pH of the mixture is adjusted to 3.5 before enzyme addition.

The viscosity was more than doubled compared to A due to the action of the endoxylanase. pH has no effect.

Effects of Fermentation

D: Lactic acid bacteria, *L. plantarum* (strain LACTOL), are added to a mixture of rye bran and water, then a 24 h fermentation at 30° C. is performed.

K: same mixture as D, wherein yeast is added 24 h after the lactic acid bacteria. A total of 48 h fermentation at 30° C. is performed.

The fermentation alone (i.e. without the incubation with the endoxylanase) does not solve the problem of providing a composition with an acceptable viscosity or with AXOS having an average DP<50.

Conditions According to the Invention

First Variant: Fermentation Before Incubation

E: Same mixture and protocol as D, except that the fermented mixture is further treated with *N. Flexuosa* endoxylanase during an incubation step of 5 h at 70° C.

This fermentation followed by incubation corresponds to a first variant according to the invention, wherein the viscosity of the obtained composition and the DP of AXOS are both optimal (i.e. viscosity lower than 150 000 cp (150 Pa s) and DP<50).

Second variant: Fermentation and Incubation are Concomitant

F: To an aqueous mixture of rye bran, lactic acid bacteria and *N. Flexuosa* endoxylanase are added. The fermentation together with the incubation are performed during 48 h at 30° C.

G: Same as F, wherein the incubation step is furthermore prolonged for 5 h at 70° C.

This concomitant fermentation and incubation corresponds to a second variant according to the invention wherein both the viscosity and the DP of AXOS are optimal (see more particularly condition F on Table 2). These conditions correspond to preferred methods and compositions of the invention.

Another Endoxylanase is Also Effective

I: same as F, with the replacement of *N. Flexuosa* endoxylanase by Belase™ B210 endoxylanase in the mixture.

J: same as I, wherein the incubation step is prolonged during 5 h at 45° C.

These conditions show that another (mesophilic) endoxylanase is also very suitable.

The addition of yeast during the fermentation with lactic acid bacteria is effective L: Aqueous mixture of rye bran and water is fermented by lactic acid bacteria and yeast, and is further treated with *N. Flexuosa* endoxylanase in an incubation step of 5 h at 70° C. A method based on fermentation with lactic acid bacteria, and yeast, and on the incubation with a endoxylanase is equally effective in providing a composition with an acceptable viscosity and average DP of AXOS.

A Third Endoxylanase Works

In another set of experiments, the condition M° is a mixture of Rye bran and water to which are added lactic acid bacteria and endoxylanase from *Pseudoalteromonas haloplanktis*. A concomitant fermentation and incubation is performed for 48 h at 25° C.

A third endoxylanase (psychrophilic) is also effective and the temperature for fermentation can be reduced to 25° C. (in order to match the optimal temperature of the endoxylanase) without being detrimental to the resulting composition.

Another Source of Grain Milling Fraction Rich in AX can be Used

N° (performed in a second set of experiments): a mixture of wheat bran and water is submitted to a fermentation for 48 h at 30° C. by lactic acid bacteria and the fermented mixture is further treated with *N. Flexuosa* endoxylanase, in the incubation step of 5 h at 70° C.

This shows that another grain milling source rich in AX can be used.

Third Variant: Incubation is Followed by Fermentation

O° (performed in a second set of experiments): a mixture of Rye bran and water is incubated with *N. Flexuosa* endoxylanase during 5 h at 70° C., then lactic acid bacteria is added for fermentation for 48 h at 30° C. (100 rpm).

In this third variant according to the invention, the incubation step precedes the fermentation and the resulting composition has both acceptable DP of AXOS and viscosity.

Example 2

Dried Composition

Compositions were prepared as described in example 1 according to the scheme of Table 3

TABLE 3

| Process steps | | | W | Y | Z |
|---|---|---|---|---|---|
| Mix | Rye bran(VK Roggen) | 140 g | X | X | X |
| | Water | 410 g | X | X | X |
| | *L. plantarum* (strain LACTOL) | 1.4 10$^9$ CFU | | | X |
| Fermentation 48 h 30° C. 100 rpm | | | | | X |
| Addition of *N. flexuosa* endoxylanase | | 0.21 ml | X | | X |
| Acidification pH 3.5 (lactic acid) | | | X | | |
| Incubation 5 h 70° C. | | | X | | X |

A sample of the compositions Y and Z were obtained and analyzed as in example 1 (samples Y and Z1). The rest of composition Z was dried using a single drum dryer with applicator rolls E 5/5 (GMF Gouda) at 10 bars steam pressure and 7 rpm speed. Sample W was too viscous to allow the drying and was not analyzed. A sample (Z2) of the dried composition was analyzed as in example 1.

Results of the analysis are presented in table 4.

TABLE 4

| | Y | Z1 | Z2 |
|---|---|---|---|
| Total AX (% DM on composition) | 19.1 | 19.3 | 19.6 |
| AXOS (% DM on composition) | 3.3 | 14.0 | 14.5 |
| DP-AX/AXOS | 273 | 8 | 11 |
| AX solubilisation (%) | 17 | 72 | 74 |

TABLE 4-continued

|  | Y | Z1 | Z2 |
|---|---|---|---|
| pH | 6.5 | 3.44 | — |
| Viscosity (Pa s) | 46.8 | 27.7 | — |

These results show that the drying step does not affect the properties of the composition and allows the development of a dry composition having a high AXOS level, a good solubilisation level and a DP allowing its prebiotic properties.

Example 3

Baked Products

Baguettes were produced using the recipe as in Table 5 (in grams):

TABLE 5

| Flour (Surbi) | 2000 | 2000 |
|---|---|---|
| Water | 1400 | 1400 |
| Fresh Yeast (Bruggeman, Belgium) | 150 | 150 |
| Sodium Chloride | 50 | 50 |
| S-500 Controller (Puratos, Belgium) | 75 | 75 |
| Sapore Traviata (Puratos, Belgium) | 60 | |
| Composition Z2 | | 60 |

* Rye-based sourdough product

The ingredients are mixed for 2 min at low and 10 min at high speed in a spiral mixer type Diosna (SP24). The final dough temperature is 26° C. After a bulk fermentation for 45 min at 25° C., 250 g dough pieces are made up using a moulder type Alliance (for 50 cm dough pieces). The dough pieces are proofed at 30° C. and 95% relative humidity for 150 min. Then the breads are baked in a rotary oven for 25 min at 230/200° C. with 7 sec steam at the oven loading and steam key open after 10 min. Same end results can be obtained by using equipment of other suppliers.

Aspect, shape, aroma and taste of the baguettes were evaluated by a sensorial taste panel. No difference in aroma and taste was perceived between the two types of baguettes.

The invention claimed is:

1. A liquid composition adapted for the preparation of baked products comprising:
   fermented grain milling fraction(s), the grain milling fraction(s) having an endogenous AX content of at least 10% (w/w) on dry matter,
   lactic acid bacteria,
   active exogenous endoxylanase,
   said composition having an AXOS content higher than 8% w:w dry matter content and having an AXOS content of 52% to 88% w:w of the total AX content of said composition, said AXOS having an average DP between 5 and 50;
   wherein said composition has a viscosity at 30° C. of lower than 100 Pa·s and a dry matter content between 18% and 50% w:w.

2. The composition of claim 1, wherein the fermented grain milling fraction(s) comprise(s) fermented cereal grain milling fraction(s).

3. The composition of claim 1 having a dry matter content between 20% and 40% w:w.

4. The composition according to claim 1 having an acidic pH.

5. The composition according to claim 1 having a dynamic viscosity (30° C.) lower than 35 Pa·s.

6. The composition according to claim 1, wherein the lactic acid bacteria are *Leuconostoc* or *lactobacilli*.

7. An improver comprising the composition of claim 1.

8. A premix or a complete mix comprising the composition of claim 1.

9. The composition of claim 1, further comprising yeast.

10. The composition of claim 1, comprising a total AX content of at least 10% w:w dry matter.

11. The composition of claim 1, comprising a total AX content of at least 15% w:w dry matter.

12. A dried composition comprising the composition of claim 1 wherein the water has been removed.

13. The composition of claim 2, wherein the fermented grain milling fraction(s) is/are fermented cereal bran.

14. The composition of claim 2, wherein the fermented grain milling fraction(s) is/are fermented wholegrain flour.

* * * * *